United States Patent
Grassle et al.

(10) Patent No.: US 9,292,656 B2
(45) Date of Patent: Mar. 22, 2016

(54) SYSTEMS AND METHODS FOR IMPROVED PERINATAL WORKFLOW

(75) Inventors: Tamara Grassle, Fox River Grove, IL (US); Dianne Kessler, Algonquin, IL (US); Charles Levecke, Cary, IL (US); Leonard Evan Kahn, Northbrook, IL (US); Afrazuddin Mohammad, Schaumburg, IL (US); John Baartz, Tower Lakes, IL (US); Jeffrey Paul Czaplewski, Chicago, IL (US); Michael Jordan, Severna Park, MD (US); Renee Vitullo, Austintown, OH (US)

(73) Assignee: General Electric Company, Schenectady, NY (US)

( * ) Notice: Subject to any disclaimer, the term of this patent is extended or adjusted under 35 U.S.C. 154(b) by 1276 days.

(21) Appl. No.: 12/970,563

(22) Filed: Dec. 16, 2010

(65) Prior Publication Data

US 2012/0075116 A1 Mar. 29, 2012

Related U.S. Application Data

(60) Provisional application No. 61/387,922, filed on Sep. 29, 2010.

(51) Int. Cl.
*G08C 19/22* (2006.01)
*G06F 19/00* (2011.01)
*G06Q 50/22* (2012.01)

(52) U.S. Cl.
CPC ............ *G06F 19/3406* (2013.01); *G06Q 50/22* (2013.01)

(58) Field of Classification Search
CPC ............................ G06F 19/3406; G06Q 50/22
USPC ............ 340/870.07, 870.01, 870.05, 870.08; 705/1.1, 3, 2, 4; 348/143, 552; 386/321, 328, 571, 578
See application file for complete search history.

(56) References Cited

U.S. PATENT DOCUMENTS

| | | | |
|---|---|---|---|
| 5,838,313 A * | 11/1998 | Hou et al. | 715/201 |
| 8,154,723 B2 * | 4/2012 | Fu et al. | 356/335 |
| 8,566,738 B2 * | 10/2013 | Van Vlimmeren | 715/772 |
| 2002/0091548 A1 * | 7/2002 | Auer et al. | 705/3 |
| 2008/0208631 A1 * | 8/2008 | Morita et al. | 705/3 |
| 2009/0183095 A1 | 7/2009 | Deitsch et al. | |
| 2010/0131293 A1 | 5/2010 | Linthicum et al. | |

* cited by examiner

*Primary Examiner* — Kerri McNally
(74) *Attorney, Agent, or Firm* — Hanley, Flight and Zimmerman, LLC

(57) ABSTRACT

Certain examples provide systems and methods for improved perinatal workflow. An example system includes a user interface to display a time continuum of live data for a selected patient. The user interface includes a compressed view of the time continuum of live data over a first time period; an expanded view of the time continuum of live data over a second time period, the second time period to be shorter than the first time period; one or more indicators to be associated with data shown in the expanded view, each indicator to indicate a point of interest in the data; a first control to change the second time period for the expanded view display; and a second control to mark an indicator with respect to the data shown in the expanded view of the time continuum of live data.

23 Claims, 11 Drawing Sheets

SYSTEMS AND METHODS FOR IMPROVED PERINATAL WORKFLOW

RELATED APPLICATIONS

The present application relates to and claims the benefit of priority from U.S. Provisional Patent Application No. 61/387,922, filed on Sep. 29, 2010, which is herein incorporated by reference in its entirety.

FEDERALLY SPONSORED RESEARCH OR DEVELOPMENT

[Not Applicable]

MICROFICHE/COPYRIGHT REFERENCE

[Not Applicable]

BACKGROUND

Perinatal systems involve a high degree of data granularity and a particular workflow for high acuity cases. Patient condition can change very rapidly so large delays in getting information into an electronic system are not acceptable.

BRIEF SUMMARY

Certain examples provide systems and methods for improved perinatal workflow.

Certain examples provide a patient monitor system providing data regarding a selected patient to a user. The system includes a memory to buffer live data received from one or more external sources for a selected patient. The system includes a user interface to display a time continuum of live data for the selected patient, the time continuum including data from a current moment to the beginning of a cycle of care for the selected patient. The user interface includes a compressed view of the time continuum of live data over a first time period; an expanded view of the time continuum of live data over a second time period, the second time period to be shorter than the first time period; one or more indicators to be associated with data shown in the expanded view, each indicator to indicate a point of interest in the data; a first control to change the second time period for the expanded view display; and a second control to mark an indicator with respect to the data shown in the expanded view of the time continuum of live data. The system includes a processor to process data for output via the user interface and to process user input.

Certain examples provide a computer-implemented method for real time monitoring of patient data. The method includes receiving live data from one or more external sources for a selected patient. The method includes displaying, via a user interface, a time continuum of live data for the selected patient, the time continuum including data from a current moment to the beginning of a cycle of care for the selected patient, the display via user interface including: a compressed view of the time continuum of live data over a first time period; an expanded view of the time continuum of live data over a second time period, the second time period to be shorter than the first time period; one or more indicators to be associated with data shown in the expanded view, each indicator to indicate a point of interest in the data; a first control to change the second time period for the expanded view display; and a second control to mark an indicator with respect to the data shown in the expanded view of the time continuum of live data. The method includes receiving and processing user input with respect to the user interface.

Certain examples include a tangible computer readable storage medium including executable program instructions which, when executed by a computer processor, cause the computer to implement a patient monitoring system providing data regarding a selected patient to a user. The patient monitoring system includes a user interface to display a time continuum of live data for a selected patient, the time continuum including data from a current moment to the beginning of a cycle of care for the selected patient. The user interface includes a compressed view of the time continuum of live data over a first time period; an expanded view of the time continuum of live data over a second time period, the second time period to be shorter than the first time period; one or more indicators to be associated with data shown in the expanded view, each indicator to indicate a point of interest in the data; a first control to change the second time period for the expanded view display; and a second control to mark an indicator with respect to the data shown in the expanded view of the time continuum of live data.

Figure 1:
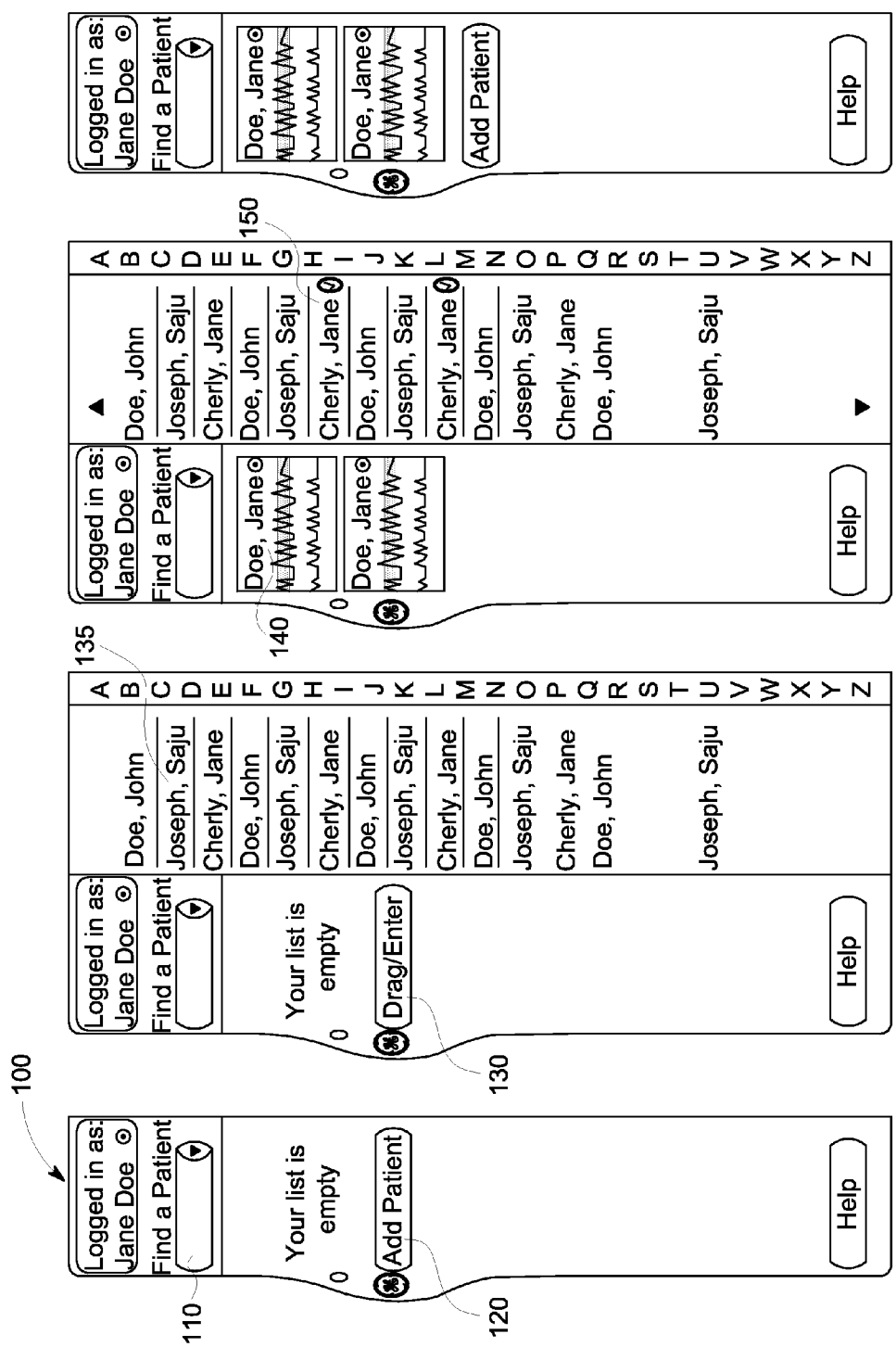
FIGS. 1-2 illustrate example dock interaction displays providing patient information to a user.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EXAMPLES

Although the following discloses example methods, systems, articles of manufacture, and apparatus including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware.

Accordingly, while the following describes example methods, systems, articles of manufacture, and apparatus, the examples provided are not the only way to implement such methods, systems, articles of manufacture, and apparatus.

When any of the appended claims are read to cover a purely software and/or firmware implementation, at least one of the elements in an at least one example is hereby expressly defined to include a tangible medium such as a memory, DVD, CD, Blu-ray, etc. storing the software and/or firmware.

Certain clinical areas, such as a high acuity perinatal department in a hospital, have a much higher ratio of clinician to patient because the clinician should be documenting continuously. Traditionally, large delay is introduced because clinicians have gloved hands and are treating a patient and must then wash their hands, get to a computer to enter information, etc. Thus, an hour or more may pass before documentation is entered. People forget information or chart it at the wrong time, and that impacts legal liability and patient treatment.

Additionally, hospitals are demanding enterprise systems, so department systems should have better interoperability with enterprise systems. Systems should help user be better and smarter in documentation. Certain examples are agnostic to any enterprise system. Certain examples help support an improved real-time perinatal workflow with additional tools, information, and capabilities. Certain examples provide sharing of a clinical (e.g., perinatal) application with other clinical applications. Certain examples provide trend navigation through clinical (e.g., perinatal) data. Certain examples provide a multi-patient sidebar view of real time and/or stored patient data. Certain examples provide a view of a time continuum and associated data along with an ability to edit, annotate, report, and retrieve information associated with a patient's time continuum.

Clinical Surveillance View

Healthcare professionals can review and document patient data in an application (e.g., a perinatal application) while monitoring various live streaming data of other patients using an overlaid user interface (UI) widget. A healthcare professional can examine a detailed view of any of the other patients' data by selecting a patient and displaying the detailed information, while switching contexts in the underlying application to allow continuous documentation.

In certain examples, upon activation, a Clinician's Surveillance View (CSV) docks or positions itself with respect to one of four sides of a monitor/display screen (e.g., against an edge of the display). When desired, the CSV can be left to float in any section of the visual display. The CSV overlays, in a non-intrusive way, an underlying application that is currently being used, which helps enable the health care professional to pursue other tasks while monitoring information in the CSV bar.

The CSV includes certain interactions and options to enable health care professionals to add and monitor patient information in real time. When necessary and/or desired, health care professionals can click on one of the patients live feeds to view additional information. When a live feed is clicked to view additional information, other background applications bring that particular patient's information into focus to add redundancy in data manipulation.

Thus, the CVS helps to prevent interruptions in usage of other systems involved in a clinical (e.g., perinatal) workflow, such as an enterprise wide system, while allowing clinicians to simultaneously (or at least substantially simultaneously given some system delay) monitor live data for multiple patients. For example, the CVS can be used in a labor and delivery environment with real-time fetal monitoring, as well as in any high-risk care area.

In certain examples, CVS can interoperate and function concurrently with enterprise wide application(s). Enterprise wide applications are generally non-specific to a particular care area, and CVS facilitates user access to functionality and rich clinical content targeted for high-risk care areas, while allowing user to continue to leverage enterprise wide systems for comprehensive documentation.

In certain examples, continuous streams of live data can be embedded within an overlaid application.

FIG. 1 illustrates an example dock interaction display 100 or "sidebar" providing a patient list and related real time waveform information to a user. The display 100 can be positioned anywhere on a display screen by a user, such as in a middle right hemisphere of a user's screen. The display 100 can interact with and/or be apart from other application(s) executing on the user's computer. As demonstrated in FIG. 1, a user can search for a patient 110, add a patient 120, drag and drop 130 patient(s) from a list 135 to be monitored, etc. Once a patient is added to the monitoring list, real time (or substantially real time including a system delay (e.g., processing, data retrieval from memory, communication, etc.)) data (e.g., fetal monitor, patient monitor, and/or other waveform data, etc.) 140 can be displayed for one or more selected patients via the display 100. Additionally, an indicator or alert 150 regarding one or more patients can be provided via the display 100.

Figure 2A:
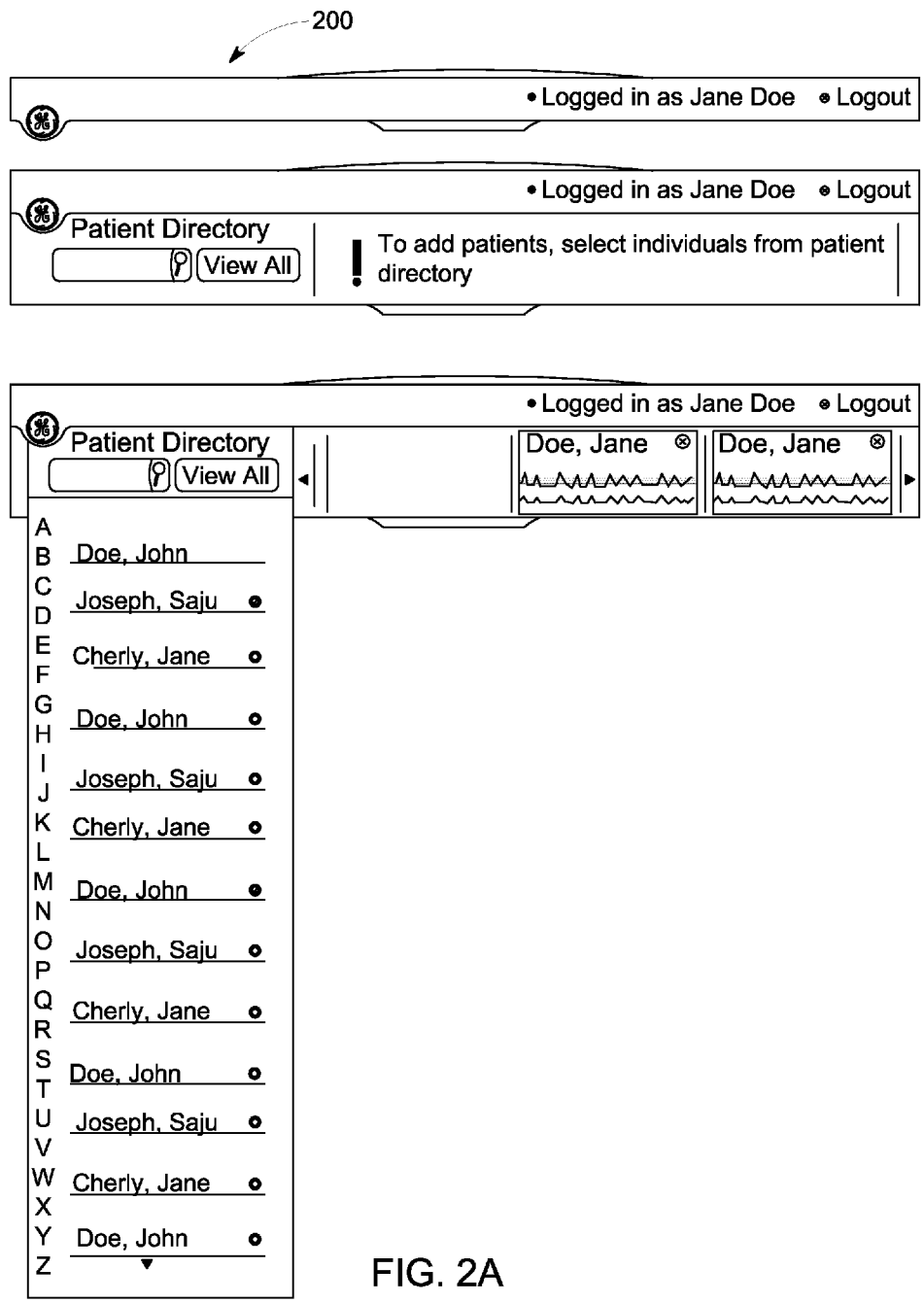
Figure 2B:
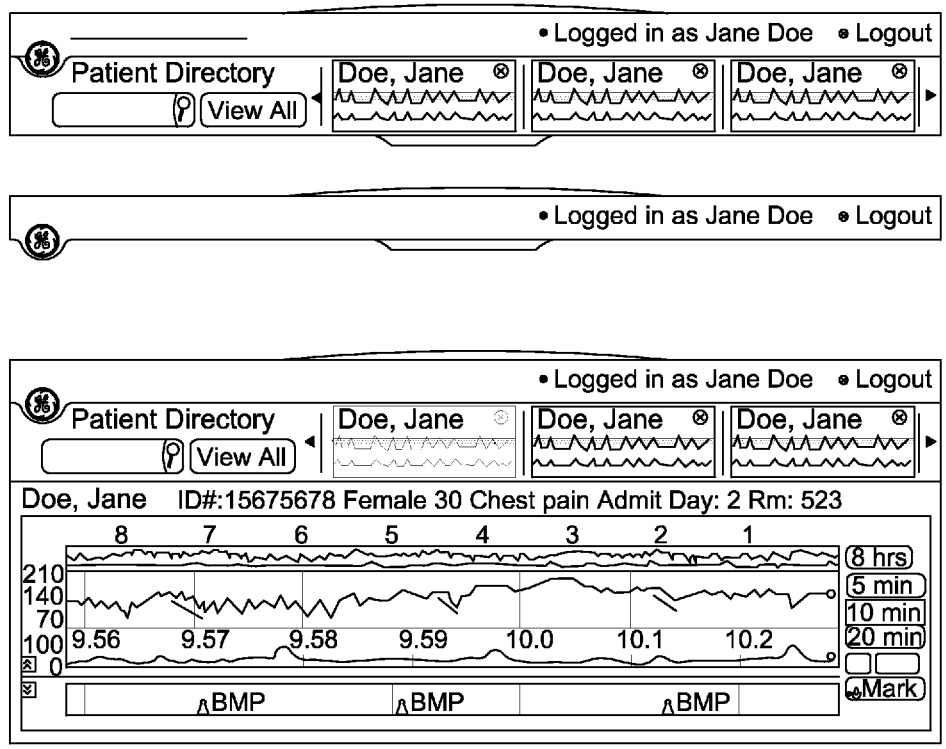

FIG. 2 illustrates another example dock interaction display 200. The example display 200 depicts how the dock display 200 may look if docked or positioned in a top hemisphere of a user's display screen.

In certain examples, using the patient sidebar or interaction display 100, 200, a user can be provided with electrocardiogram (EKG) and/or other live streaming waveform data for selected patient(s). Color-coded alerting can be provided. A user can select a patient in the sidebar 100, 200 to see a more detailed patient view. Live active scrolling can be provided.

In certain examples, a voice-activated "mark" button can be provided in conjunction with the waveform data to allow a user to document in real-time (or substantially real time) through keyboard input, mouse selection, voice indication, foot pedal, etc., to make a mark and/or other annotation on the "live" waveform. In certain examples, a mark can be automatically converted into an annotation.

Figure 3:
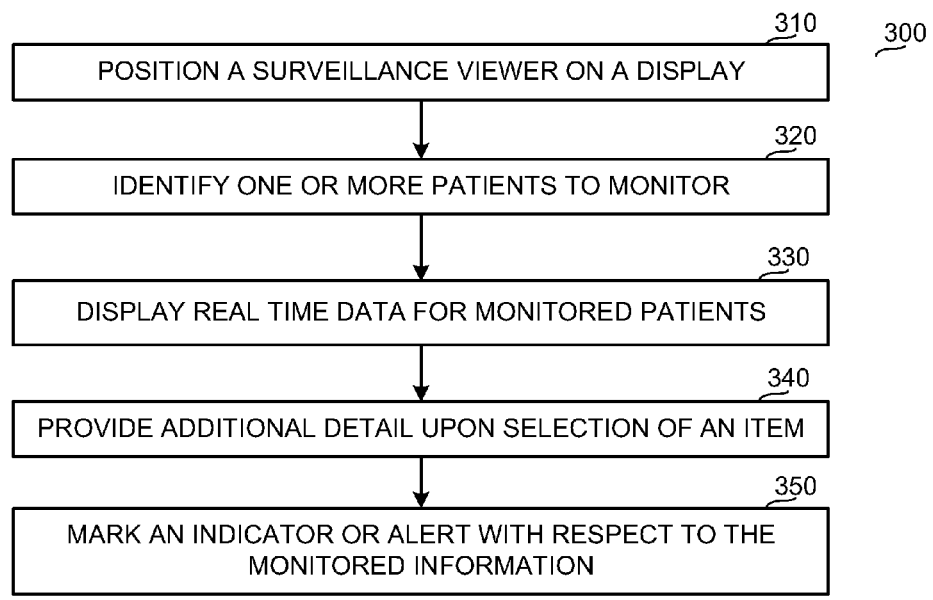
FIG. 3 depicts a flow chart for an example method for providing a clinical surveillance view of patient data to a user.

FIG. 3 depicts a flow chart for an example method 300 for providing a clinical surveillance view of patient data to a user. At 310, a surveillance viewer is positioned on a user's display. For example, the viewer can automatically (e.g., based on a default position, user-specified preference, concurrent application(s) executing, workflow, etc.) be positioned and/or manually be positioned by a user on the display. The viewer overlays, in a non-intrusive way, one or more underlying application(s) currently in use on the display. Thus, a user can interact with other applications in a patient care workflow while monitoring information in the surveillance viewer.

At 320, one or more patients to be monitored are identified. For example, a user can search for a patient. For example, a user can provide a patient name and/or browse a list of available patient(s) to identify one or more patients to be monitored. At 330, real time (e.g., including substantially real time) data for the patient is displayed to the user via the surveillance viewer. For example, fetal waveform, patient EKG, blood pressure, and/or other data can be displayed via a live feed to the user in the surveillance viewer. For example, the surveillance monitor can be used in a labor and delivery environment with real-time fetal monitoring, as well as in any other high-risk care area.

At 340, additional detail is provided upon selection of monitored data. For example, when a live feed (e.g., a fetal waveform) is clicked on, "moused" or hovered over, or otherwise selected to view additional information, that particular information is retrieved for display and/or brought into focus for the user.

At 350, an indicator or alert can be marked via the surveillance viewer. For example, an indicator or mark can be provided for a patient, a data feed, etc., for display via the surveillance viewer.

Clinical Time Continuum at Point of Care

Alternatively and/or in addition, certain examples enable a visualization of directly and indirectly acquired clinical content plotted over time and perpetually updated. Features of the visualization include co-location of clinically relevant content collected from disparate sources, supplemented by a mechanism to initiate annotations (e.g., assessments and/or actions), through which a user can indicate, preserve, and/or visualize an intended association with the content that motivated the annotation.

Additionally, certain examples provide for initiation of recording by an external recording device (e.g., audio, video, etc.), at a point of care, in order to reconstitute annotations for formal documentation at a later time.

Certain examples provide a continuously updating graph including time as the x axis to plot direct observations. Indirect observations are rendered on the same timeline, presenting a visual indicator of source and, potentially, a summary of content.

As observations are collected, a support engine processes observations to discover pattern(s) of potential correlation. Patterns are based on interpreting the values of collected observations and deducing where annotations may be appropriate, for example. These pattern discoveries are displayed on the graph as indicators of potential annotation opportunity (ies).

Recorded annotations maintain an association to pattern sources, for example. The association can indicate a target concern to which an annotation applies. These concerns can be composites of specific discrete observations, associated with a range of time, and/or with a series of time ranges, for example. Additionally, users can initiate annotations and explicitly define their own observation dependency(ies), by selecting and highlighting either a range of time which includes known content, or by explicitly multi-selecting specific content (e.g., CTRL-CLICK), for example.

By setting context (e.g., via hover/mouse over, click/select, etc.) on a previously noted annotation, associated clinical content can be exposed. Proposed exposition can include a bubble web from the annotation whereby the associated content is encircled and a connection line is drawn, for example. Associations based strictly on time range can highlight a relevant range on the graph, for example.

In certain examples, audio/visual recording can be initiated to invoke a record action. The visual can then display the start of the record mode and its duration. The completion of the record mode results in the preservation of the recording as a clinical observation and the creation of a proposed annotation (as noted above), with the recording as the associated content.

Often, high-acuity clinical settings such as labor and delivery, suffer from inefficiency and lack of timely documentation. Care and safety of a patient is a top priority above clinical documentation of that care. However, timeliness of that documentation leads to increased accuracy and availability of data for review by other clinicians. For example, if a nurse is caring for a patient during delivery, he/she will be wearing gloves and other protective equipment. The nurse will be unable to document using a keyboard or mouse until he/she can remove the gloves. The nurse also will be unable to document in a system if a patient has immediate needs such as turning onto side or starting a drip of intravenous (IV) fluids. Certain examples allow a user to tag a time continuum using an input device such as keyboard/mouse, voice command/control, etc.

Additionally, clinicians may be interested in reviewing correlated data as the data becomes available to a clinician. A clinician might not be aware that data is available or might have to search through multiple sources to correlate different data inputs (such as lab data, with vitals data, with fetal strip data, etc.). Because a clinician can see the data correlated on one screen from multiple external sources, the clinician can now more efficiently review the data, make inferences from that data, and document interactions associated with a group of data elements on a time continuum.

Certain examples provide a new level of usability for a live patient encounter and bedside documentation. Data representation facilitates contextual interaction against a patient record at a specific point in time. Centralized visualization of different sources of data is provided on a patient time-continuum in a single application. The patient time continuum organization and display allows for correlation of other series/sources of data to provide further evidence of an event and its related annotation. The time continuum display also enhances recognition of associative relationships by providing visual indicators.

Alternatively, flowsheets can be used to record content over time. However, flowsheets are significantly more ridged in structure (having time bound to known intervals as columns). This consumes a significant amount of lateral real estate.

Certain examples allow for direct documentation upon a continuous waveform. Furthermore, other clinical observations over time, such as XDS document awareness, lab messages, etc., can be documented and displayed upon the continuous waveform. Associative relationships, as well as visual co-location, of the data can also be facilitated.

Rather than relied on paper printouts from fetal monitors that must be manually written on, electronic fetal waveform capture with electronic annotations allow the content to be stored in a discoverable and searchable format. Recordings can be automatically and/or manually initiated, for example. In certain examples, hyperlinks can allow traversal of associated content through data association(s).

Figure 4:
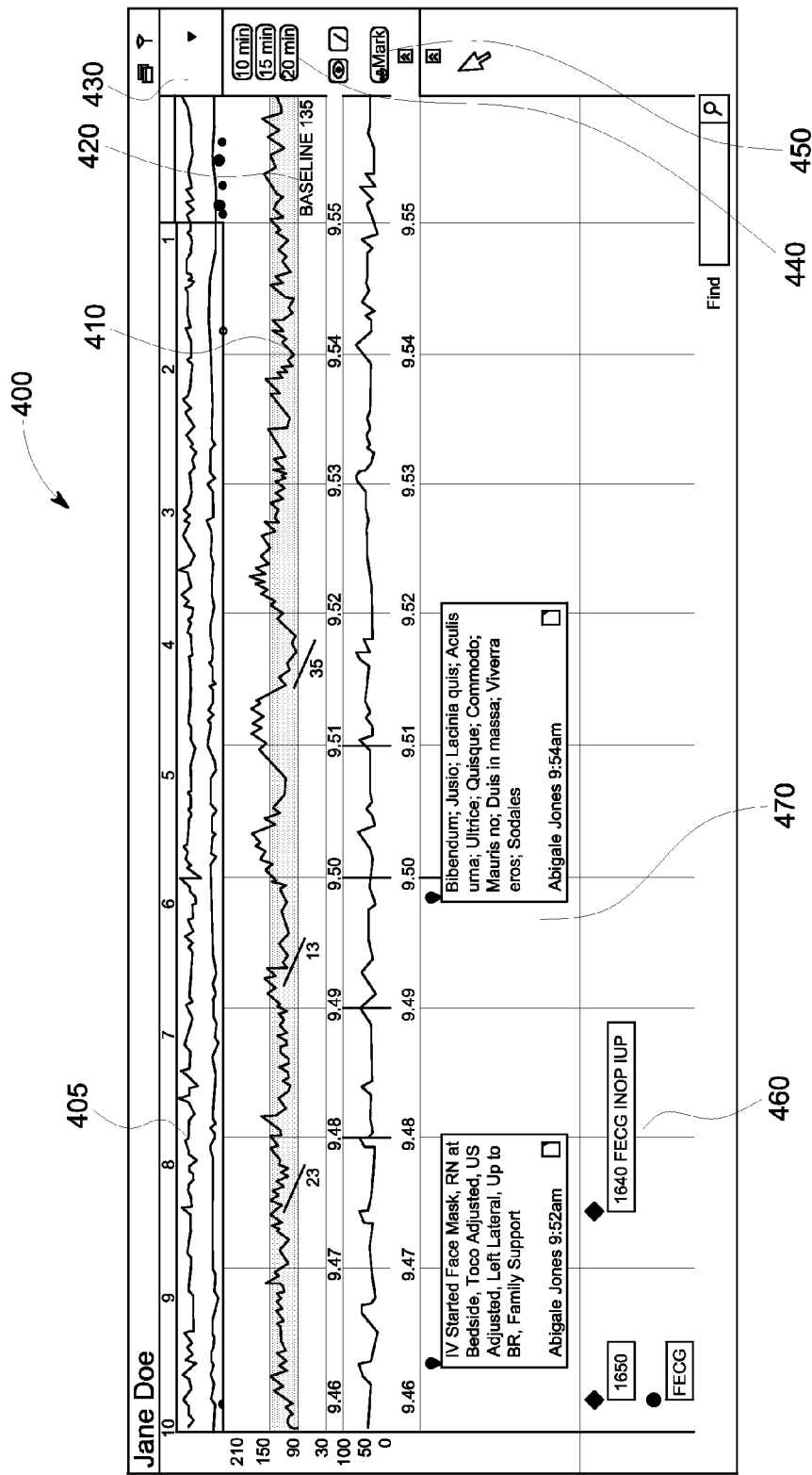
FIG. 4 illustrates an example viewer providing a time continuum and associated information for a monitored patient.

FIG. 4 illustrates an example viewer 400 providing a time continuum and associated information for a monitored patient. The viewer 400 conveys indications of monitored waveform data 410 provided against a baseline 420 for a patient. The waveform data 410 represents a portion of a time continuum 405 for the patient (e.g., an expanded portion compared to a compressed overall view of the time continuum 405). As illustrated in FIG. 4 the time continuum 405 can provide a window 430 (e.g., an eight hour window) in a current care cycle for the patient, while the waveform data 410 represents a current live feed or another selected subset of that data. The waveform data window 410 can provide a certain time subset 440 determined automatically and/or specified by a user (e.g., looking back five minutes, ten minutes, twenty minutes, etc.). One or more controls 450 allow a user to overlay data, mark data, insert annotations or notes, etc. As represented in FIG. 4, automatic (e.g., system or derived) annotations 460 as well as user-input annotations 470 can be shown and interacted with via the viewer 400.

Using the viewer 400, a user documents with respect to a point of care as the user is providing care and ties the documentation to the time continuum 405. This information can be provided (e.g., automatically and/or manually) into a flowsheet and/or other format to be viewed and/or correlated with other information (e.g., a vital signs graph, EKG waveform, lab results, etc.) so that the information all appears in the time continuum 405. Information can be tied together and provided in a visual format, so that, for example, a user can see a last lab result when a patient's EKG dropped. The user can open the lab result and superimpose a vital signs graph and see the information together for evaluation. Information can be provided in real-time (including substantially in real time), not after the fact (like a longitudinal record).

In certain examples, the time continuum 405 can stretch from the current moment to the beginning of a cycle of care (e.g., the start of pregnancy). For example, the time continuum 405 may include two hours of test, then have no data for two weeks, then include a hospital visit, etc. In certain examples, a user can track everything done in the time continuum and can select and review individual items in more detail. The time continuum 405 can be presented chronologically based on occurrence, chronologically based on time of documentation, etc. The viewer 400 can provide different ways to analyze a story and recreate what happened, for example.

In certain examples, data can be provided to a mobile device (e.g., a tablet computer, smart phone, laptop, netbook, personal digital assistant, etc.). For example, voice commands can be provided via a wired or wireless connection (e.g., Bluetooth, Wi-Fi, etc.) and a user can review information on the mobile, etc. In certain examples, the mobile device can perform at least some of the processing for dictation, etc. Using the mobile device, a user can document "on the fly" as he or she moves a patient from a waiting room to an operating room, for example. Data can also be captured during transport from hospital to hospital and documentation maintained in transit to complete the patient record, for example.

In certain examples, a user may have other data not tied to the time continuum that he or she wants to see in the same space, but separate from the time continuum (e.g., a labor curve, vitals, growth curve, normal ranges, etc.). The viewer 400 can provide a separate axis for such information (e.g., an axis showing four hours of data versus fifteen minutes of waveform data).

In certain examples, the viewer 400 provides a real-time (including substantially real time) push of updated information/content (e.g., lab results, etc.) that "pops up" or appears for a user to see as the user is documenting and treating a patient in real time. In certain examples, the viewer 400 can be pre-configured to quickly provide information to a user that he or she can popup in the time continuum 405 and then close to resume patient charting. For example, the user can view the popup data but does not have to pull the data item(s) into their time continuum.

In certain examples, the viewer 400 is provided as a "floating" window that is always on top and always available with other applications visible and accessible underneath. In certain examples, a compressed view can be provided on top of the floating window to see trending over a long period of time without having to scroll through data, for example.

In certain examples, the time continuum 405 can be searched by keyword and navigated to a location or locations for a corresponding annotation (or annotations). In certain examples, a user can grab or otherwise select a tab and navigate forward and/or backward through available data. The time continuum 405 and other information in the viewer 400 can include flags, indicators, and/or other pointer to data, events, and/or other information, for example.

Figure 5:
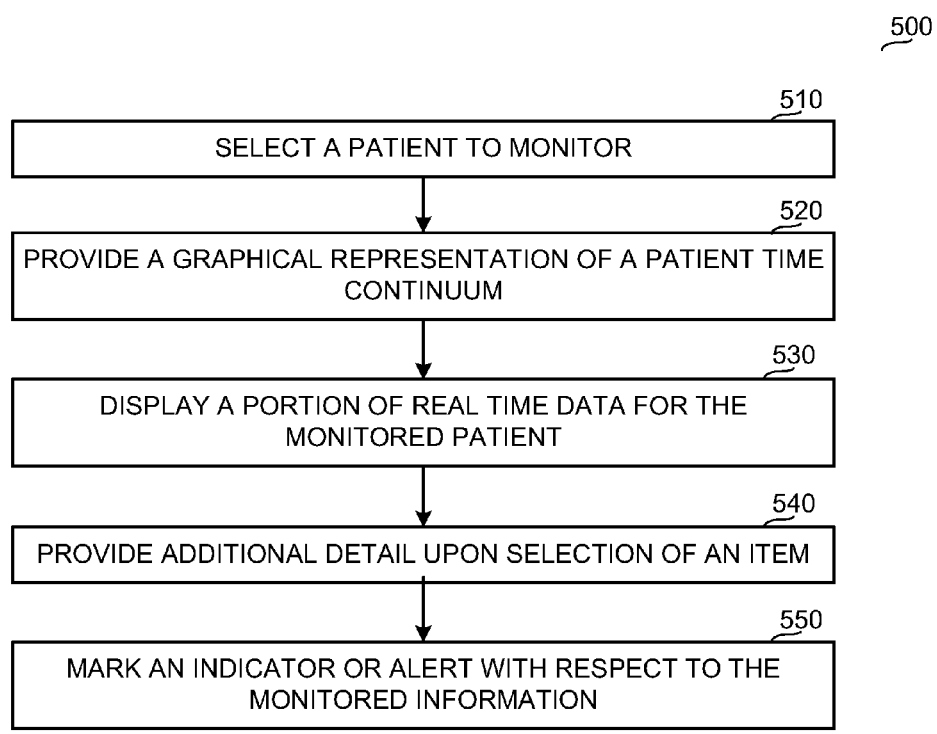
FIG. 5 depicts a flow chart for an example method for providing a clinical time continuum and associated real time data for a patient to a user.

FIG. 5 depicts a flow chart for an example method 500 for providing a clinical time continuum and associated real time data for a patient to a user. At 510, a patient is selected for monitoring and viewing via a time continuum viewer. At 520, a time continuum of data for the patient over a specified period is graphically represented via the viewer. At 530, a real time or live portion (including substantially real time) of the time continuum data is displayed via the window. For example, the past ten minutes of the patient's EKG waveform are displayed in greater detail apart from the overall time continuum. The time continuum and the portion continue to update in real time (including substantially real time).

At 540, additional detail is provided upon selection of monitored data. For example, when a live feed (e.g., a fetal waveform) is clicked on, "moused" or hovered over, or otherwise selected to view additional information, that particular information is retrieved for display and/or brought into focus for the user.

At 550, an indicator or alert can be marked via the surveillance viewer. For example, an indicator or mark can be provided for a patient, a data feed, etc., for display via the surveillance viewer.

Clinical Charting Using Voice and/or Video

Clinicians often need to record information quickly and store this data in a patient's electronic medical record (EMR) and/or other data store. By utilizing tools such as dictation voice recognition and video monitoring of patient care, clinical data entry into the EMR and/or other data store can be automated.

In certain examples, a clinical system (e.g., a perinatal system) can include a voice and video recognition engine embedded in the software and/or hardware to capture audio and/or video content and identify pertinent data elements and events in recorded data. For example, captured audio can be parsed and spoken data matched to discrete EMR data elements, while also noting a time index in the recording for quick recall and playback.

For example, as a clinician provides care for a patient, audio and, optionally, video can be recorded, analyzed and parsed to identify clinical data elements to be stored in the patient's EMR. Recordings can run continuously, or can be started and stopped at the clinician's discretion using a voice command, or other physical toggle (e.g., foot pedal, keyboard, mouse, etc.). A time continuum can be updated with an indicator to show a time at which data capture was initiated.

A parsing and recognition system can identify discrete data elements in audio and/or video and classify the data elements using standard terminology (e.g., SNOMED, ICD-9, ICD-10, NANDA, etc.) and/or hospital provided terminology for storage in the patient's EMR.

As elements are parsed, each discrete set of elements is indexed based on time in the recording. The recorded session of care, as well as the parsed data, are saved for later authentication and accuracy verification. After the audio and/or video data is analyzed, a clinician is presented with a user interface screen on a computer showing a list of discrete elements and corresponding values as interpreted or actions performed. The user interface facilitates user authentication and verification of the parsed data, for example. The user interface can display a confidence level, determined by an analysis engine, for the data presented. In certain examples, each element and/or value includes a link to a specific time slice in the recording that is associated with the analyzed data.

The clinician can use this link to quickly replay the relevant portion of the recording and see or hear the information again for verification. Access to the complete recorded session can be made available for context if requested.

The analysis engine and user interface with indexed replay option allow clinicians to provide patient care while the system (e.g., a perinatal system) records the pertinent clinical data to the EMR quickly and accurately.

Thus, while clinicians are busy taking care of their patients, it is very difficult to document at the same time care is being given. There are often critical events that are time sensitive, and it is important that the clinician can record the data at the time of the event, while simultaneously providing patient care. Dictating a quick comment or a "mark" of some type can assist a clinician (e.g., a nurse) to accurately document events as they occur (and/or shortly thereafter). For example, a nurse who has gloved hands and cannot touch a keyboard can dictate, "head delivered" in a perinatal application. Analysis of video can document actions performed such as "patient was moved to side position". The nurse can then go back after the event and confirm and/or add to his/her documentation, for example.

Thus, certain examples facilitate faster and more accurate charting of patient data. Using dictation and dictation parsing, validation of the parsed data can be facilitated to provide more accurate patient records in a more efficient manner. Additionally, in some examples, video recordings can also be analyzed and parsed to identify clinical data elements. A user interface and workflow for quickly validating that information.

Figure 6:
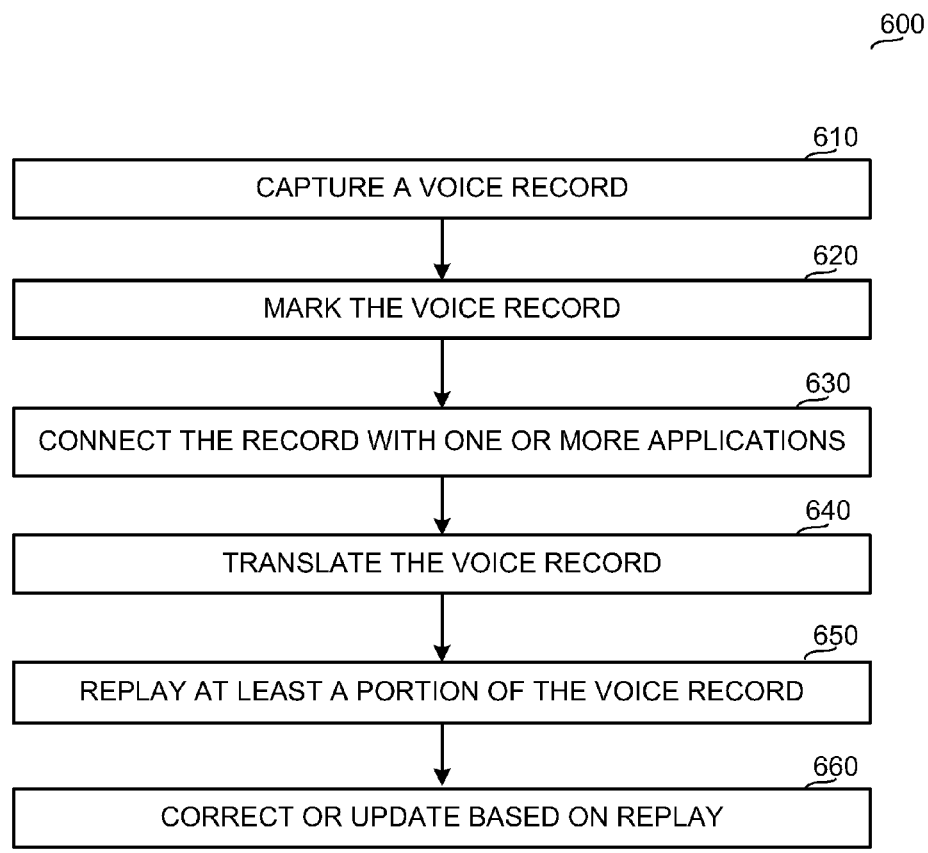
FIG. 6 depicts a flow chart for an example method for voice recording, playback, and integration with a patient record.

FIG. 6 depicts a flow chart for an example method 600 for voice recording, playback, and integration with a patient record. At 610, a voice record is captured. For example, a voice record is captured via real time (including substantially real time) dictation. At 620, the voice record is marked. For example, the voice record is automatically and/or manually marked with one or more time stamps, segment(s), keyword (s), etc. At 630, the voice record is connected with one or more applications used by the user. For example, the voice record is inserted into a time continuum and/or patient record associated with a patient. At 640, the voice record is translated (e.g., via a speech to text conversion). At 650, a user can replay the stored voice record. For example, the user can replay an entire voice record, a marked field of the voice record, a selected section of the voice record, etc., to allow a clinician to replay and confirm/correct determined values from a speech to text translation of the voice record. At 660, one or more values can be corrected/updated based on the reviewed recording. Thus, voice recording and playback helps facilitate an improved workflow with applications, voice dictation capture, user review, reporting, etc.

Figure 7:
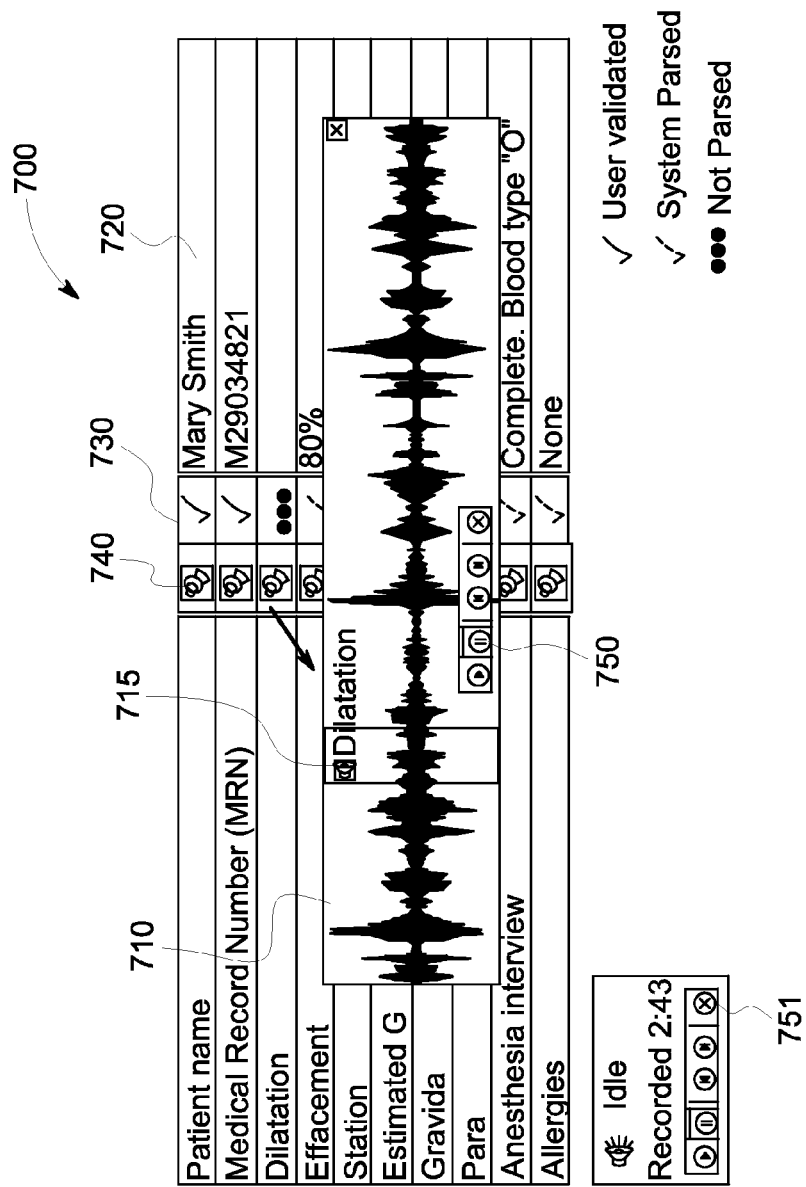
FIG. 7 illustrates an example voice recording and review interface.

Certain examples provide clinicians with a more efficient mechanism to receive and record information while providing patient care. FIG. 7 illustrates an example voice recording and review interface 700. As shown in FIG. 7, audio data 710 can be parsed and made visible 720 for validation by a user. Audio can be made available for replay during a validation phase, for example. Voice data can be played back, translated into a note, etc. Video data can be similarly provided.

In certain examples, a summary of information can be provided by a clinician and/or patient and spoken without having to type into a computer.

In certain examples, dictation can be parsed into discrete values, and the discrete values 720 can be displayed and provided outbound to corresponding clinical documentation. For example, a nurse's comment "Heartrate 120" is translated and parsed to determine that the field is "heartrate" and the value for that field is "120". In certain examples, after a voice recording has been mapped to fields and values, a confidence index and/or status 730 can be provided to a user. The user can then replay 740, approve 730, change, and/or store a value, for example. The user can replay 740 an entire recording, a certain portion 715 (e.g., keyword or section), etc., of the voice data 710, for example. Voice playback can be started, stopped, paused, forwarded, reversed, etc., using one or more controls 750-751, for example.

Voice charting helps a user receive patient history and details as a clinician enters a room with the patient. A user can dictate exam results without paper or computer available (e.g., via mobile device). A viewer and/or reporting tool can prompt the user for missing exam details and/or other items and provide visual indicators and/or alerts to the user, for example. Using mobile dictation and reporting, a clinician can visit multiple patients before stopping at the computer for further documentation and analysis.

In certain examples, an audio and/or visual notification can be provided to user when lab or other results are ready. Audio and/or visual notification can also be used to provide reminders for patient care.

"Smart" Clinical Annotations

In certain examples, users are able to enter clinical annotations (e.g., documented observations, events, alerts, etc.) in a structured format by giving values to specified data items with a time context. In certain examples, a system presents the user with a pre-defined set of items to annotate. Additionally, the system includes a capability to learn a clinical state of the patient, alter a user interface presented to the user, and modify workflows in the user experience (UX) appropriately. The system and associated method(s) integrate both manually documented and acquired data to recognize a state or condition of the patient. The state can represent a phase of care (e.g., pre-operative versus intra-operative phases in a surgical unit), some clinical progression (e.g., antepartum, labor, delivery, postpartum stages in a labor and delivery unit), and/or other patient status (e.g., a postpartum patient who has delivered a girl versus one who has delivered a boy). As the patient's state changes, the nature of information presented to and recorded by the end user changes to reflect the current patient state.

Certain examples provide systems and methods to recognize patient state and adapt presented information accordingly. The state can be a function of a single documented item including a certain expected value or being within some expected range, for example. The state can be defined by a group of items including expected values. The state can depend upon a chronological order of the recording of a group of variables, for example. A patient can also occupy multiple states concurrently. A set of rules can be configured to define the identified states.

For example, a labor and delivery (L&D) patient may have four (4) states —antepartum, labor, delivery, and postpartum. A system can inspect whether the patient has had documented contraction intervals of five (5) minutes or less, any dilatation value less than ten (10) centimeters (cm) is recorded, and is admitted to a bed in an L&D unit. If all conditions are true, then the system recognizes that the patient is in labor. Similarly, if a patient is in the postpartum state, the system can recognize that she has delivered a boy or a girl depending on the charted gender. At this point, she is assigned one state based upon the fact that she delivered and another state based upon the delivery and the baby's gender. Another example involves a patient who is in the delivery state at the same time she is in a C-section state (versus natural delivery state).

In certain examples, the user experience is altered streamline documentation and reduce errors. Continuing the previous example, the patient may appear differently in a roster once the system recognizes the labor state. The system can also add or remove certain documentation capabilities based upon the state. In the example, once a patient has entered the post-partum/girl delivery state, the user no longer has an option to chart that the baby was circumcised. If a patient is in the natural delivery state, the user will be unable to chart any information related to performance of a C-section, for example. Thus, available annotation options can be provided, removed, limited, and/or otherwise guided based on patient state and other available patient data, for example.

In certain examples, systems and methods used for clinical documentation, often in a high-paced environment in which clinicians are caring for multiple patients at the same time. Awareness of patient state allows a system to streamline workflows, presenting users with only pertinent options for use and documentation at given state(s). Thus, less time can be spent doing the work of documentation and more time spent attending to the patient. Additionally, by only allowing a user to record appropriate information, inconsistencies and errant conflicts in the record can be minimized or prevented.

Streamlining nurse workflow allows nurses and/or other healthcare practitioners to spend more time interacting with their patients and less time documenting on the computer. Additionally, error reduction is provided by lessening clinical risk and legal liability in the case of inaccurate information being stored in the patient's record.

In certain examples, inconsistencies can also be reported after documentation is complete. Post-hoc examination can identify specific data items that conflict with each other.

In certain examples, a rules engine can be applied to infer a patient state. In certain examples, multiple states can be applied to a patient at the same time. In certain examples, sub-states and/or combination states (e.g., state delivered+ state girl=state delivered girl) can be provided. In certain examples, documented items from external data sources (e.g., external information systems via interface, fetal monitor, other devices, etc.) can be examined by a system to determine state.

In certain examples, a user can also explicitly specify a patient state to confirm, correct, or override an automated system determination of state. The system can then provide intelligent documentation capabilities based upon the declared state.

Figure 8:
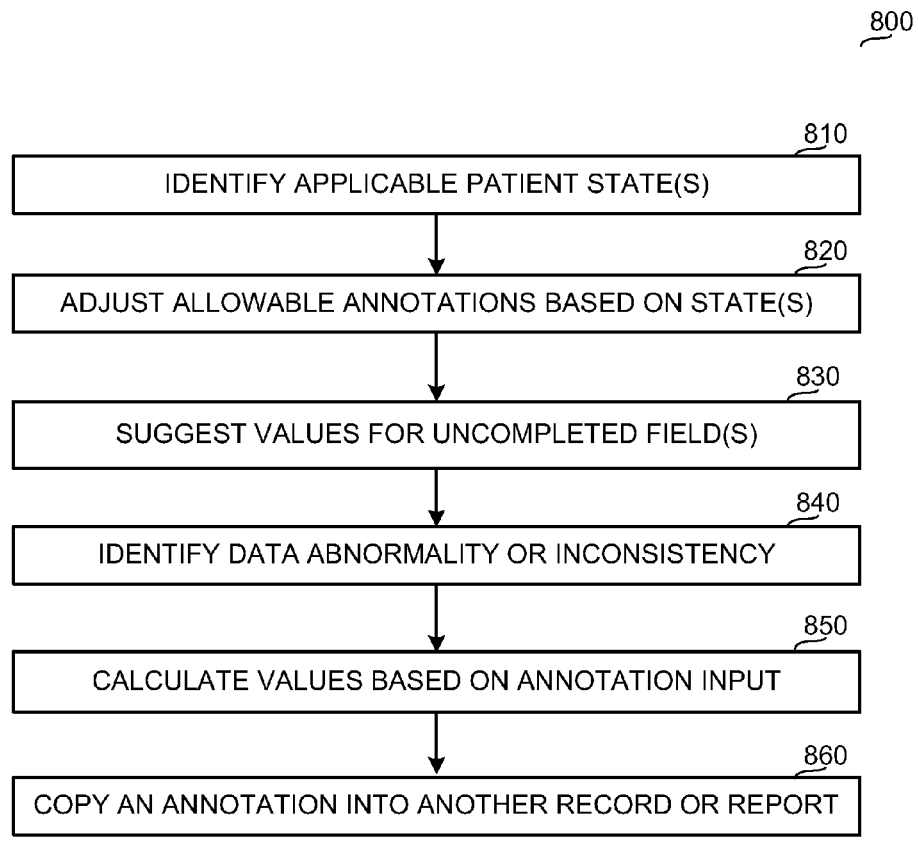
FIG. 8 illustrates a flow chart for an example method for smart clinical annotation of patient information in a clinical workflow.

FIG. 8 illustrates an example method 800 for smart clinical annotation of patient information in a clinical (e.g., perinatal) workflow. At 810, one or more applicable patient states are identified. For example, one or more states indicative of patient condition, patient status, patient treatment, etc., are automatically identified based on stored patient data (e.g., EMR data, personal health record (PHR) data, radiology information system (RIS) data, picture archiving and communication system (PACS) data, etc.).

At 820, based on patient state(s), allowable annotations made by a user on a patient record are adjusted. For example, as a user is charting that a patient is eight (8) cm dilated, the type of available annotations is automatically adjusted to be more related to baby delivery than if the user were annotating that the patient is two (2) cm dilated.

At 830, based one or more completed fields, values are suggested for remaining fields. For example, a user begins to input information into a field and values can then be suggested for one or more remaining fields based on the existing input and a historical data store of annotations.

At 840, data abnormalities or inconsistencies are identified. For example, data that does not make sense given other provided data is flagged. For example, a user cannot chart about a circumcision when the baby is a girl. In certain examples, certain choices may not be provided to a user based on the other information available. Based on this "smart", more efficient charting, error can be reduced or prevented. Clinical decision support and rules can be used to support such "smart" charting.

At 850, values are calculated automatically based on annotation input. The calculated values can form part of an annotation and/or can be approved by a user and placed into a patient record and/or report. For example, an annotation of a waveform can automatically trigger a waveform analysis that is pulled into an annotation. For example, a user can mark a fifteen (15) minute window and values can be calculated based on that marked window. The automatically calculated values can be approved and dropped into a record.

At 860, an annotation can be selected and copied into another annotation, record, and/or report. For example, recent documentation can be selected and copied by a user into another annotation, patient record, report, etc.

Figure 9:
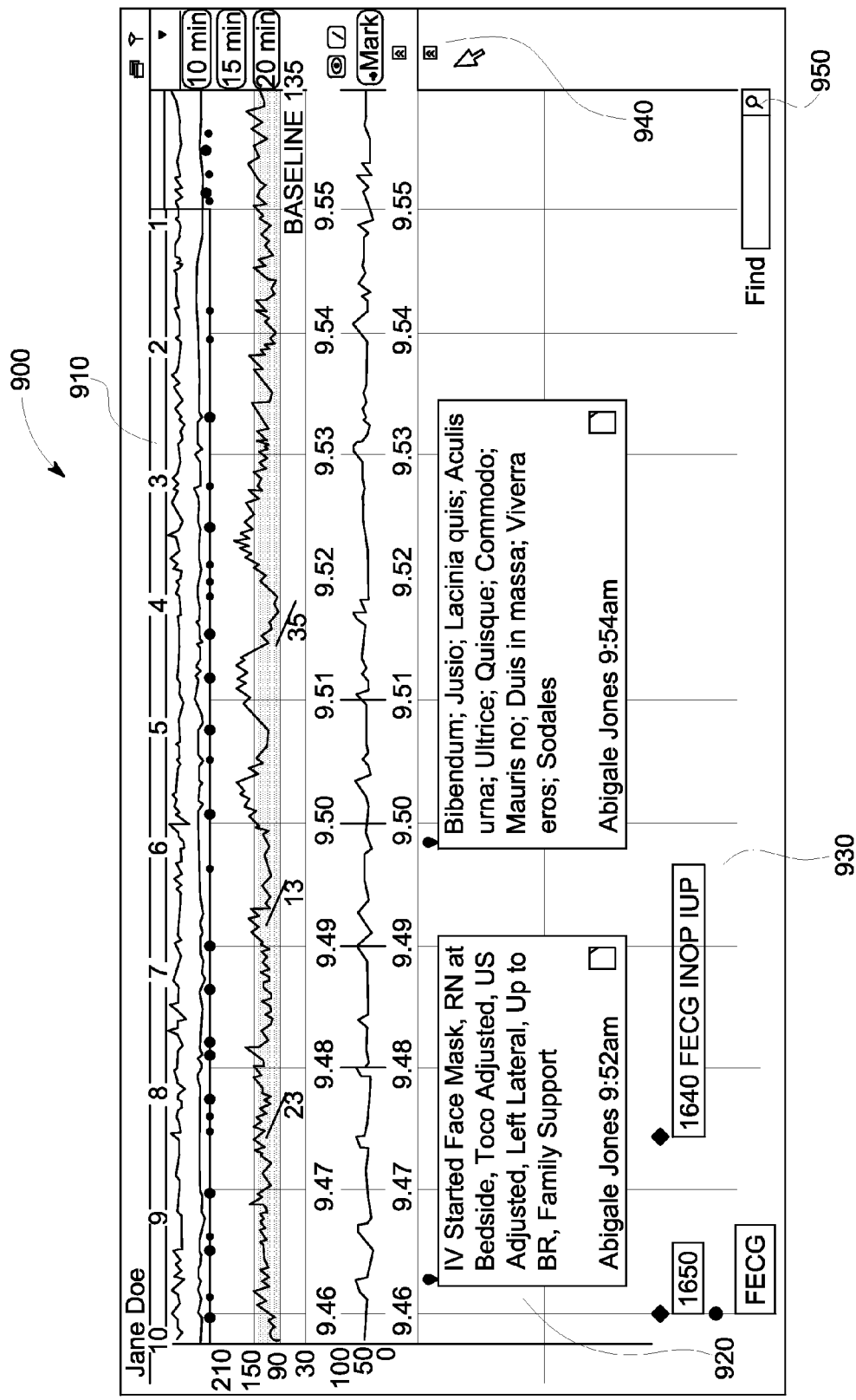
FIG. 9 illustrates an example interface for annotation review.

FIG. 9 illustrates an example interface 900 for expanded annotation review. The annotation review 900 includes clinical data 910 for a patient, clinician annotation(s) 920, system or automatically generated/determined annotation(s) 930, and one or more controls including a collapse/expand control 940, a search control 950, etc.

FIGS. 3, 5, 6, and 8 are flow diagrams representative of example machine readable instructions that may be executed to implement example systems and methods described herein, and/or portions of one or more of those systems (e.g., systems 100 and 1100) and methods. The example processes of FIGS. 3, 5, 6, and 8 can be performed using a processor, a controller and/or any other suitable processing device. For example, the example processes of FIGS. 3, 5, 6, and 8 can be implemented using coded instructions (e.g., computer readable instructions) stored on a tangible computer readable medium such as a flash memory, a read-only memory (ROM), and/or a random-access memory (RAM). As used herein, the term tangible computer readable medium is expressly defined to include any type of computer readable storage and to exclude propagating signals. Additionally or alternatively, the example processes of FIGS. 3, 5, 6, and 8 can be implemented using coded instructions (e.g., computer readable instructions) stored on a non-transitory computer readable medium such as a flash memory, a read-only memory (ROM), a random-access memory (RAM), a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Alternatively, some or all of the example processes of FIGS. 3, 5, 6, and 8 can be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIGS. 3, 5, 6, and 8 can be implemented manually or as any combination(s) of any of the foregoing techniques, for example, any combination of firmware, software, discrete logic and/or hardware. Further, although the example processes of FIGS. 3, 5, 6, and 8 are described with reference to the flow diagrams of FIGS. 3, 5, 6, and 8, other methods of implementing the processes of FIGS. 3, 5, 6, and 8 can be employed. For example, the order of execution of the blocks can be changed, and/or some of the blocks described can be changed, eliminated, sub-divided, or combined. Additionally, any or all of the example processes of FIGS. 3, 5, 6, and 8 can be performed sequentially and/or in parallel by, for example, separate processing threads, processors, devices, discrete logic, circuits, etc.

Figure 10:
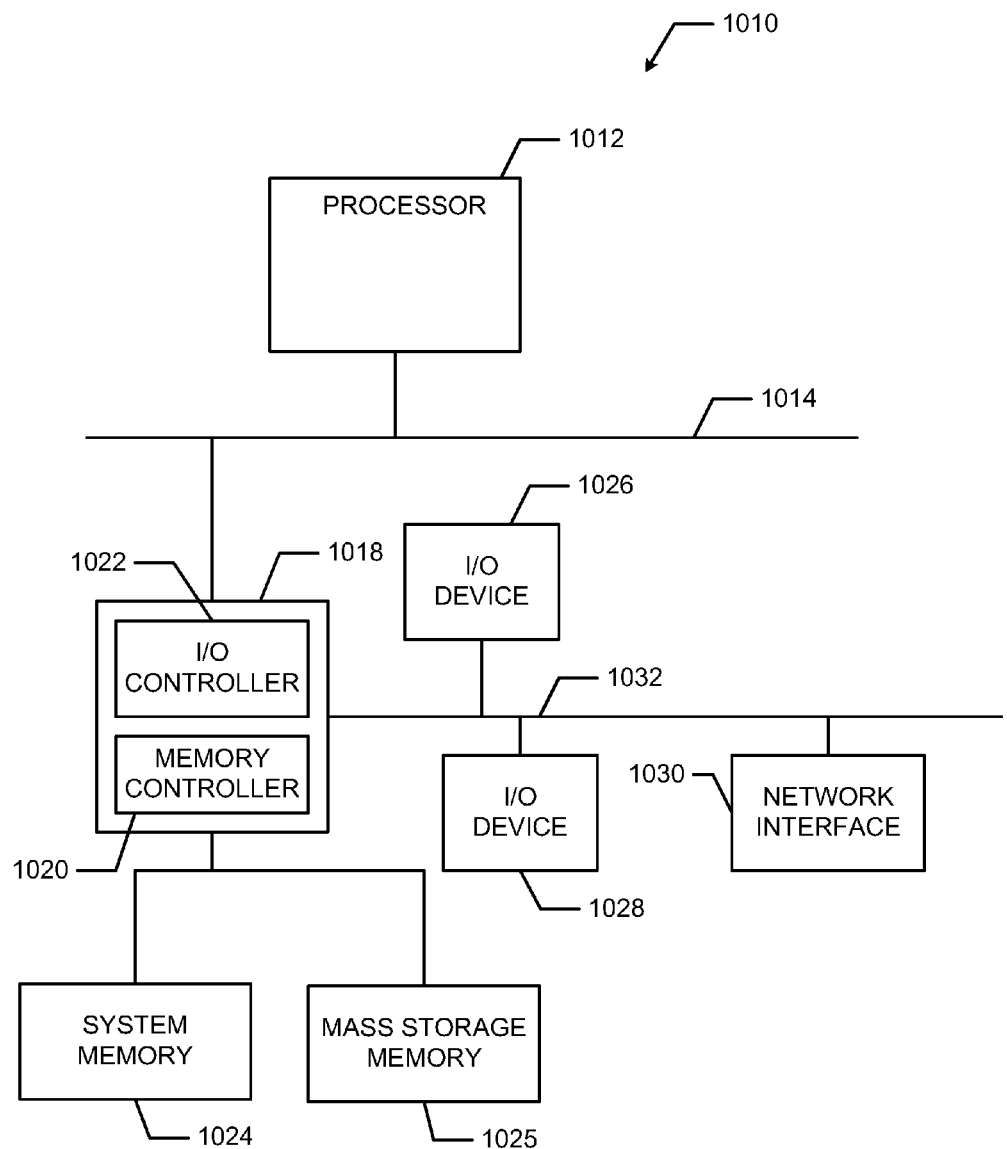
FIG. 10 is a block diagram of an example processor system that can be used to implement the systems, apparatus and methods described herein.

FIG. 10 is a block diagram of an example processor system 1010 that can be used to implement the systems, apparatus and methods described herein. As shown in FIG. 10, the processor system 1010 includes a processor 1012 that is coupled to an interconnection bus 1014. The processor 1012 can be any suitable processor, processing unit or microprocessor. Although not shown in FIG. 10, the system 1010 can be a multi-processor system and, thus, can include one or more additional processors that are identical or similar to the processor 1012 and that are communicatively coupled to the interconnection bus 1014.

The processor 1012 of FIG. 10 is coupled to a chipset 1018, which includes a memory controller 1020 and an input/output (I/O) controller 1022. As is well known, a chipset typically provides I/O and memory management functions as well as a plurality of general purpose and/or special purpose registers, timers, etc. that are accessible or used by one or more processors coupled to the chipset 1018. The memory controller 1020 performs functions that enable the processor 1012 (or processors if there are multiple processors) to access a system memory 1024 and a mass storage memory 1025.

The system memory 1024 may include any desired type of volatile and/or non-volatile memory such as, for example, static random access memory (SRAM), dynamic random access memory (DRAM), flash memory, read-only memory (ROM), etc. The mass storage memory 1025 may include any desired type of mass storage device including hard disk drives, optical drives, tape storage devices, etc.

The I/O controller 1022 performs functions that enable the processor 1012 to communicate with peripheral input/output (I/O) devices 1026 and 1028 and a network interface 1030 via an I/O bus 1032. The I/O devices 1026 and 1028 may be any desired type of I/O device such as, for example, a keyboard, a video display or monitor, a mouse, etc. The network interface 1030 may be, for example, an Ethernet device, an asynchronous transfer mode (ATM) device, an 802.11 device, a DSL modem, a cable modem, a cellular modem, etc. that enables the processor system 1010 to communicate with another processor system.

While the memory controller 1020 and the I/O controller 1022 are depicted in FIG. 10 as separate blocks within the chipset 1018, the functions performed by these blocks may be integrated within a single semiconductor circuit or may be implemented using two or more separate integrated circuits.

Thus, certain examples provide one or more floating windows or "always available" viewers providing streaming, real time, or "live" data to a user regarding one or more of his/her patients. Data can include fetal and/or patient waveform data, patient time continuum, voice record, annotations, reports, etc. The floating viewer can be combined, separated, etc., and positioned at any location on a user's display. Certain examples provide rules-based limitations and/or assistance regarding annotations, reporting, charting, etc. Certain examples provide speech to text conversion for review, playback, and inclusion in annotations, reports, charting, etc.

Certain examples contemplate methods, systems and computer program products on any machine-readable media to implement functionality described above. Certain examples can be implemented using an existing computer processor, or by a special purpose computer processor incorporated for this or another purpose or by a hardwired and/or firmware system, for example.

One or more of the components of the systems and/or steps of the methods described above may be implemented alone or in combination in hardware, firmware, and/or as a set of instructions in software, for example. Certain examples can be provided as a set of instructions residing on a computer-readable medium, such as a memory, hard disk, DVD, or CD, for execution on a general purpose computer or other processing device. Certain examples can omit one or more of the method steps and/or perform the steps in a different order than the order listed. For example, some steps/blocks may not be performed in certain examples. As a further example, certain steps may be performed in a different temporal order, including simultaneously, than listed above.

Certain examples include computer-readable media for carrying or having computer-executable instructions or data structures stored thereon. Such computer-readable media can be any available media that may be accessed by a general purpose or special purpose computer or other machine with a processor. By way of example, such computer-readable media can include RAM, ROM, PROM, EPROM, EEPROM, Flash, CD-ROM, DVD, Blu-ray, optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Certain examples can be practiced in a networked environment using logical connections to one or more remote computers having processors. Logical connections can include a local area network (LAN) and a wide area network (WAN) that are presented here by way of example and not limitation. Such networking environments are commonplace in office-wide or enterprise-wide computer networks, intranets and the Internet and can use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Examples can also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain examples or embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment or example disclosed, but that the invention will include all embodiments falling within the scope of the description and appended claims.

The invention claimed is:

1. A patient monitor system providing data regarding a selected patient to a user, said system comprising:
   a memory to buffer live data received in a real time data stream from one or more external sources for a selected patient;
   a user interface to display a time continuum of live data retrieved from the memory for the selected patient, the time continuum including data from a current moment to the beginning of a cycle of care for the selected patient, the user interface including:
      a compressed view of at least a first portion of the time continuum of live data over a first time period;
      an expanded view of at least a second portion of the time continuum of live data over a second time period, the second time period to be shorter than the first time period;
      one or more indicators to be associated with data shown in the expanded view, each indicator to indicate a point of interest in the data, each indicator to set an alert with respect to the point of interest in the data;
      a first control to change the second time period for the expanded view display; and
      a second control to mark each of the one or more indicators with respect to the data shown in the expanded view of the at least second portion of the time continuum of live data, wherein the second control is to facilitate annotation of the time continuum of live data provided in the expanded view, the second control to assist the user in completing an annotation and to evaluate input from the user according to a criterion related to at least one of the data in the expanded view and patient information; and
   a processor to process the time continuum of live data, the compressed view, the expanded view, and the one or more indicators for output via the user interface and to process user input via the first control and second control.

2. The system of claim 1, wherein the expanded view of the time continuum of live data is to include monitored waveform data provided against a baseline for the selected patient.

3. The system of claim 1, wherein the second control is to allow the user to at least one of overlay data, mark data, and insert an annotation with respect to the time continuum of live data in the expanded view.

4. The system of claim 3, wherein an annotation inserted by the user is to be associated with the time continuum of live data in a report.

5. The system of claim 1, wherein the input includes selection of a portion of the time continuum data and wherein evaluation of the input includes an automated calculation of a value associated with the selected portion, the value to be added as an annotation of the selected portion.

6. The system of claim 5, wherein the annotation of the selected value is to be automatically added to a report by the processor.

7. The system of claim 1, wherein the first control comprises a control for voice marking and playback, wherein the processor is to parse voice recording from the first control into discrete values for storage and playback in association with selected data from the expanded view of the time continuum of live data.

8. The system of claim 7, wherein the voice input is to be converted to an annotation and added to a report by the processor.

9. The system of claim 7, wherein a confidence index is to be generated in association with the parsing of the voice recording into a discrete value.

10. The system of claim 7, wherein the first control is to facilitate replay of a portion of the voice recording based on an index associated with the parsed voice recording.

11. A computer-implemented method for real time monitoring of patient data comprising:
   receiving live data in a real time data stream from one or more external sources for a selected patient;
   displaying, via a user interface, a time continuum of live data received in the real time data stream for the selected patient, the time continuum including data from a current moment to the beginning of a cycle of care for the selected patient, the display via user interface including:
      a compressed view of at least a first portion of the time continuum of live data over a first time period;
      an expanded view of at least a second portion of the time continuum of live data over a second time period, the second time period to be shorter than the first time period;
      one or more indicators to be associated with data shown in the expanded view, each indicator to indicate a point of interest in the data, each indicator to set an alert with respect to the point of interest in the data;
      a first control to change the second time period for the expanded view display; and
      a second control to mark each of the one or more indicators with respect to the data shown in the expanded view of the at least second portion of the time continuum of live data, wherein the second control is to facilitate annotation of the time continuum of live data provided in the expanded view, the second control to assist the user in completing an annotation and to evaluate input from the user according to a criterion related to at least one of the data in the expanded view and patient information; and
   receiving and processing user input via the first control and the second control with respect to the user interface.

12. The method of claim 11, wherein the expanded view of the time continuum of live data is to include monitored waveform data provided against a baseline for the selected patient.

13. The method of claim 11, wherein the second control is to allow the user to at least one of overlay data, mark data, and insert an annotation with respect to the time continuum of live data in the expanded view.

14. The method of claim 13, associating an annotation inserted by the user with the time continuum of live data in a report.

15. The method of claim 11, wherein the input includes selection of a portion of the time continuum data, and wherein evaluating the input includes automatically calculating a value associated with the selected portion, and adding the value as an annotation of the selected portion.

16. The method of claim 15, further comprising automatically adding the annotation of the selected value to a report.

17. The method of claim 11, wherein the first control comprises a control for voice marking and playback, and wherein the method further comprises parsing a voice recording from the first control into discrete values for storage and playback in association with selected data from the expanded view of the time continuum of live data.

18. The method of claim 17, further comprising converting the voice recording to an annotation and adding the annotation to a report.

19. The method of claim 17, further comprising generating a confidence index in association with the parsing of the voice recording into a discrete value.

20. The method of claim 17, further comprising facilitating replay of a portion of the voice recording based on an index associated with the parsed voice recording.

21. A non-transitory computer readable storage medium including executable program instructions which, when executed by a computer processor, cause the computer to implement a patient monitoring system providing data regarding a selected patient to a user, said patient monitoring system comprising:
   a user interface to display a time continuum of live data received in a real time data stream for the selected patient, the time continuum including data from a current moment to the beginning of a cycle of care for the selected patient, the user interface including:
      a compressed view of at least a first portion of the time continuum of live data over a first time period;
      an expanded view of at least a second portion of the time continuum of live data over a second time period, the second time period to be shorter than the first time period;
      one or more indicators to be associated with data shown in the expanded view, each indicator to indicate a point of interest in the data, each indicator to set an alert with respect to the point of interest in the data;
      a first control to change the second time period for the expanded view display; and
      a second control to mark each of the one or more indicators with respect to the data shown in the expanded view of the at least second portion of the time continuum of live data, wherein the second control is to facilitate annotation of the time continuum of live data provided in the expanded view, the second control to assist the user in completing an annotation and to evaluate input from the user according to a criterion related to at least one of the data in the expanded view and patient information.

22. The computer readable medium of claim 21, wherein the first control comprises a control for voice marking and playback, wherein the processor is to parse voice recording from the first control into discrete values for storage and playback in association with selected data from the expanded view of the time continuum of live data.

23. The computer readable medium of claim 21, wherein the input includes selection of a portion of the time continuum data and wherein evaluation of the input includes an automated calculation of a value associated with the selected portion, the value to be added as an annotation of the selected portion.

* * * * *